Sept. 30, 1969 P. ECKE Plant Pat. 2,925
POINSETTIA PLANT
Filed Feb. 27, 1968
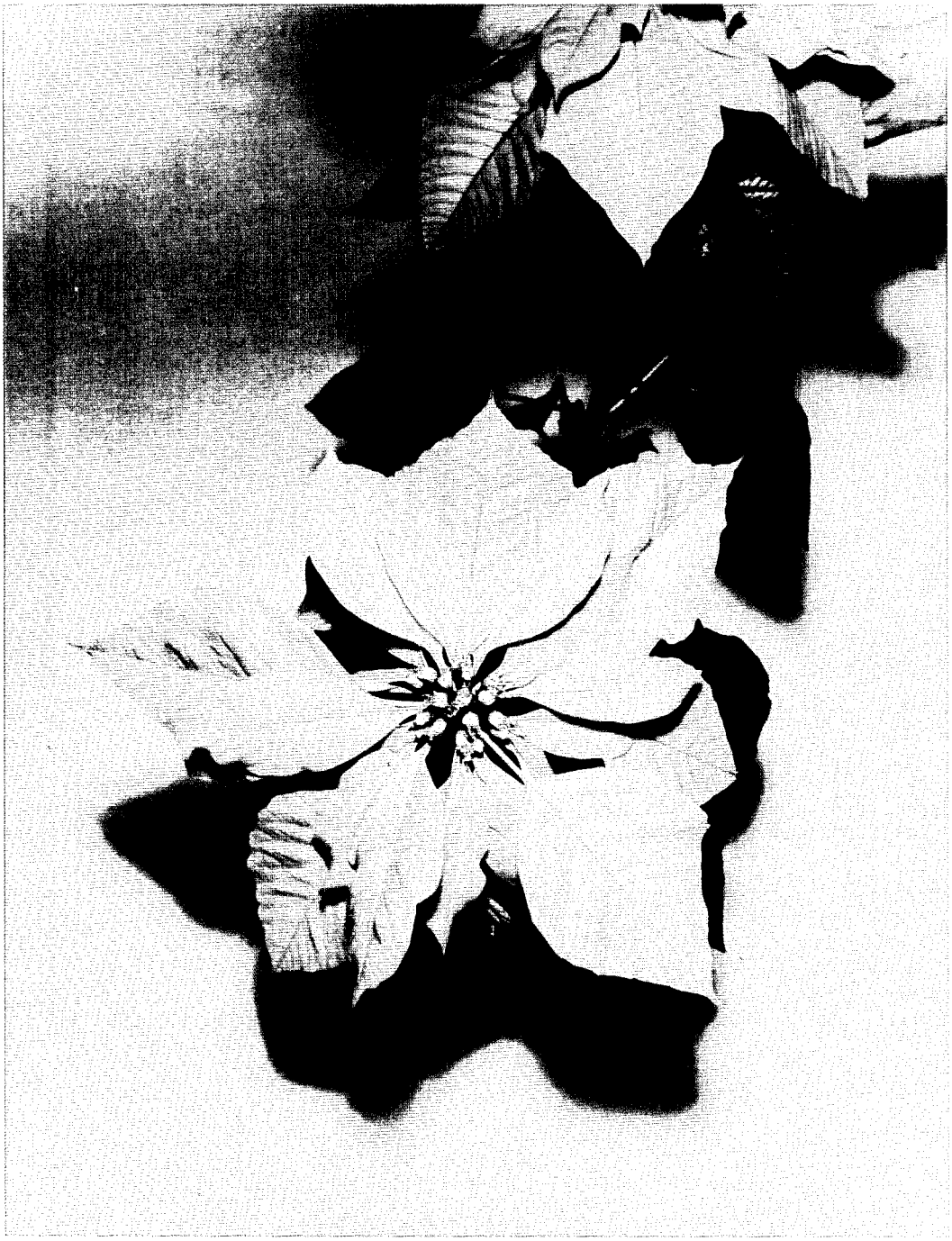
Inventor.
Paul Ecke
By: Robb & Robb
Attorneys.

United States Patent Office

Plant Pat. 2,925
Patented Sept. 30, 1969

2,925
POINSETTIA PLANT

Paul Ecke, Encinitas, Calif., assignor to Paul Ecke, Inc., Encinitas, Calif., a corporation of California Filed Feb. 27, 1968, Ser. No. 708,730
Int. Cl. A01h 5/12
U.S. Cl. Plt.—86 1 Claim The present invention relates to a new and distinct variety of poinsettia plant (botanically known as *Euphorbia Pulcherrima*), which was originated by me by crossing the poinsettia variety known as "Stoplite" (unpatented) with an unnamed and unpatented red poinsettia seedling, the former being the seed parent and the latter being the pollen parent The primary objectives of this breeding were to produce an early blooming variety having a new and different color heretofore unknown in early blooming commercial varieties, while retaining the wide bracts and full appearance of the long lasting varieties. These objectives fully achieved along with other desirable features, as evidenced by the following unique combination of characteristics which are outstanding in the new variety and which distinguish it from its parents, as well as from all other varieties of which I am aware:

(1) A vary vigorous, tough and durable plant habit;
(2) Stiff stems which do not require staking;
(3) A very vigorous and extensive root system;
(4) An early blooming habit, usually 9 weeks after start of short days, but having the ability to be satisfactorily brought into bloom and full maturity in every month of the year through the exercise of proper greenhouse cultural techniques;
(5) A medium height but vigorous growing habit when grown naturally;
(6) The ability to pinch well;
(7) Well defined, very wide bracts surrounding a rather tight center, giving a particularly attractive, symmetrical appearance;
(8) A distinctive and attractive, slightly ruffled appearance of the bracts and their absence of any tendency to droop with age;
(9) A distinctive and attractive general color tonality of the bracts corresponding to Geranium Lake;
(10) Absence of drooping and retention of the inflorescence position relative to the bracts without rising as occurs in other varieties as the inflorescence approaches maturity;
(11) A suitability for the production of multiple bloom plants; and
(12) Excellent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Encinitas, Calif., under regular commercial practices:

Parentage: Seedling.
*Seed parent.*—"Stoplite."
*Pollen parent.*—An unnamed red seedling.

Propagation: Holds its distinguishing characteristics through succeeding propagations by vegetative cuttings.

Form: Medium tall; upright.

Habit of growth: Very vigorous; medium upright.

Rooting Habit: Fast (from 15–20 days under mist); vigorous; extensive; uniform.

Blooming habit: Approximately 9 weeks after start of short days.

Blooming season: Can be satisfactorily brought into bloom in every month of the year by appropriate greenhouse culture practices.

Foliage: Alternate; borne horizontally on stems; persistent; normal quantity.
*Size.*—Medium (from about 3 inches to 7 inches long); width from about 2½ inches to 4 inches.
*Shape.*—Arrowhead.
*Texture.*—Upper side—semi-glossy; ordinary recessed veins. Under side—Dull; ordinary protruding veins.
*Margin.*—Well defined.
*Color.*—New foliage: upper side—near Scheele's Green, Plate 860, page 175. Lower side—near Scheele's Green, Plate 860, page 175. Old foliage: upper side—near Ivy Green, Plate 0001060/2, page 200; lower side—near Spinach Green, Plate 0001060/3, page 200.

Disease resistance: Resistant to rhizoctonia and pythium stem and root rot during propagation and growing period, and resistant to botrytis during blooming period, as determined by comparison with other plants grown under the same cultural conditions at Encinitas, Calif., which are infected with these diseases.

Bracts: Many (approximately 20 to 25 in number); very wide; well defined; medium length; new bracts form and develop as other bracts mature; normal lasting qualities; short-pointed when young, but becoming very wide at maturity; retain relative position and do not droop when mature or as bracts continue to age; normal color retention; slightly ruffled in appearance; have short petioles giving a full appearance. Color: upper side—near Geranium Lake, Plate 20/2, page 20; under side—near Rose Opal, Plate 022/1, page 110.

Flowers:
*Borne.*—Many flowers per stem in regular clusters in varying stages of development; borne on strong, short stems; slow development, giving a compact appearance; position of flowers remains relatively low without rising as it does in other commercial poinsettia varieties during early development, and does not spread out during later stages of development.
*Quantity of bloom.*—Relatively abundant; flowers gradually drop off after maturity, but new ones continue to develop as flower stems continue to grow.
*Buds.*—From small to medium size; borne on light green stems. Color—near Lettuce Green, Plate 861/3, page 109.

Reproductive organs:
*Stamens.*—Few; from about ⅛ inch to ¼ inch long. Color—near Claret Rose, Plate 021/1, page 109.
*Pollen.*—Near Naples Yellow, Plate 403, page 121.
*Styles.*—Color—near Rose Opal, Plate 022, page 110.
*Ovaries.*—Color—near Lettuce Green, Plate 861/2, page 176.
*Nectar cups.*—Color—near Egyptian Buff, Plate 407, page 122.

General observations: As compared with its seed parent "Stoplite," the new variety principally differs from this parent in that the new variety is pink in color whereas the parent is red; and it has smaller bracts and a tighter center than its seed parent. As compared to its unnamed pollen parent, the new variety principally differs from the parent in that it has a shorter habit of growth and its color is pink, whereas the pollen parent is taller and is red in color.

I claim:

1. A new and distinct variety of poinsettia plant, substantially as herein shown and described, characterized particularly as to novelty by the unique combination of a very vigorous, tough, and durable plant habit, stiff stems which do not require staking, a very vigorous and extensive root system, an early blooming habit, usually 9 weeks after start of short days, but having the ability to be satisfactorily brought into bloom and full maturity in every month of the year through the exercise of proper greenhouse cultural techniques, a medium height but vigorous growing habit when grown naturally, the ability to pinch well, well defined very wide bracts surrounding a rather tight center, giving a particularly attractive, symmetrical appearance, a distinctive and attractive, slightly ruffled appearance of the bracts and their absence of any tendency to droop with age, a distinctive and attractive general color tonality of the bracts corresponding to Geranium Lake, absence of drooping and retention of the inflorescence position relative to the bracts without rising as occurs in other varieties as in the inflorescence approaches maturity, a suitability for the production of multiple bloom plants, and excellent suitability for home decoration.

No references cited.

ROBERT E. BAGWILL, Primary Examiner